(12) United States Patent
Gupta

(10) Patent No.: US 8,187,467 B2
(45) Date of Patent: May 29, 2012

(54) PARENTERAL ADMINISTRATION OF PYROPHOSPHATE FOR PREVENTION OR TREATMENT OF PHOSPHATE OR PYROPHOSPHATE DEPLETION

(76) Inventor: Ajay Gupta, Cerritos, CA (US)

(*) Notice: Subject to any disclaimer, the term of this patent is extended or adjusted under 35 U.S.C. 154(b) by 825 days.

(21) Appl. No.: 11/028,114

(22) Filed: Dec. 30, 2004

(65) Prior Publication Data

US 2005/0142212 A1    Jun. 30, 2005

Related U.S. Application Data

(60) Provisional application No. 60/481,840, filed on Dec. 30, 2003.

(51) Int. Cl.
*A61K 33/42* (2006.01)
*B01D 61/26* (2006.01)
*B01D 61/24* (2006.01)

(52) U.S. Cl. ........ 210/647; 210/646; 210/645; 424/601; 424/603

(58) Field of Classification Search .................. None
See application file for complete search history.

(56) References Cited

U.S. PATENT DOCUMENTS

| | | | |
|---|---|---|---|
| 6,689,275 B1 * | 2/2004 | Gupta ............... | 210/647 |
| 6,779,468 B1 * | 8/2004 | Gupta ............... | 210/647 |
| 2007/0148258 A1 * | 6/2007 | O'Neill et al. ......... | 424/601 |

FOREIGN PATENT DOCUMENTS

| WO | WO 9829434 A1 * | 7/1998 |
|---|---|---|
| WO | WO 2005/044189 | 10/2004 |

OTHER PUBLICATIONS

U.S. Appl. No. 60/515174, specification.*
U.S. Appl. No. 60/515174, drawings.*
Anghileri, L., "Soft Tissue Calcification Induced by Iron Complexes," *Calcif. Tissue Int.* vol. 51, pp. 83-81, (1992).
Brunelli, S.M. et al., "Hypophosphatemia: Clinical Consequences and Management," *J. Am. Soc. Nephrol.*, vol. 18, pp. 1999-2003 (2007).
Fleisch, H. et al., "The Influence of Pyrophosphate Analogues (Diphosphonates) on he Precipitation and Dissolution of Calcium Phosphate In Vitro and In Vivo," *Calc. Tiss. Res.*, vol. 2, Suppl. pp. 10-10A, (1968).
Fleisch, H.A. et al., "The Inhibitory Effect of Phosphonates on the Formation of Calcium Phosphate Crystals In Vitro and on Aortic and Kidney Calcification In Vivo," *Europ. J. Clin. Invest.*, vol. 1, pp. 12-18, (1970).
Russell, R. et al., "Pyrophosphate and Diphosphonates in Calcium Metabolism and Their Possible Role in Renal Failure," *Arch. Intern. Med.*, vol. 124, pp. 571-577 (1969).
Jung, A. et al., "Fate of Intravenously Injected Pyrophosphate-$^{12}$P in Dogs," *Am. J. Physiol.*, vol. 218(6), pp. 1757-1764, (1970).
Gupta, A. et al., "Dialysate Iron Therapy: Infusion of Soluble Ferric Pyrophosphate Via the Dialysate During Hemodialysis," Kidney International, vol. 55, 1999, pp. 1891-1898.

* cited by examiner

*Primary Examiner* — Krishnan S Menon
(74) *Attorney, Agent, or Firm* — Price Heneveld LLP

(57) ABSTRACT

Phosphate depletion, a physiological condition commonly seen in certain patient populations, including alcoholics, malnourished, acutely ill patients, patients receiving parenteral nutrition, patients being re-fed after prolonged fasting, and dialysis patients, requires intravenous supplementation when oral repletion is not feasible. This invention provides a method and pharmaceutical composition for therapeutic administration of pyrophosphate, instead of phosphate, for phosphate or pyrophosphate repletion. During hemodialysis or peritoneal dialysis significant removal of phosphate and pyrophosphate occurs. Pyrophosphate depletion predisposes patients to vascular calcification. This invention further provides a method and pharmaceutical composition for therapeutic administration of pyrophosphate for phosphate or pyrophosphate repletion by addition of pyrophosphate to hemodialysis or peritoneal dialysis solutions.

6 Claims, No Drawings

PARENTERAL ADMINISTRATION OF PYROPHOSPHATE FOR PREVENTION OR TREATMENT OF PHOSPHATE OR PYROPHOSPHATE DEPLETION

CROSS-REFERENCE TO RELATED APPLICATIONS

Applicant claims benefit of the Provisional Application entitled "Parenteral Administration of Pyrophosphate For Prevention Or Treatment Of Phosphate Or Pyrophosphate Depletion" that was filed on Dec. 30, 2003 and has Application No. 60/481,840.

STATEMENT REGARDING FEDERALLY SPONSORED RESEARCH & DEVELOPMENT

No Federally sponsored research & development was used in making this invention.

FIELD OF THE INVENTION

The present invention relates to a method and composition for treatment of phosphate or pyrophosphate depletion in a mammal.

BACKGROUND

Phosphate depletion is commonly seen in certain patient populations including alcoholics, malnourished, acutely ill patients, patients receiving parenteral nutrition, patients being re-fed after prolonged fasting, or dialysis patients. Oral repletion of phosphate may not be feasible if the patient is not able to eat, suffers from malabsorption or has continuing losses of phosphate that cannot be adequately treated by the oral route. In such clinical situations phosphate is commonly administered intravenously. This invention provides a method and pharmaceutical composition for administering pyrophosphate for the prevention or treatment of phosphate or pyrophosphate depletion.

Specifically, in patients with kidney failure, excess removal of phosphate and pyrophosphate anions can occur during hemodialysis or peritoneal dialysis. Depletion of these anions from tissues and plasma leads to disorders of bone and mineral metabolism including osteomalacia and calcification of soft tissues and bone disease.

Kidneys are integral to maintenance of normal bone and mineral metabolism including excretion of phosphate. Patients with kidney failure are unable to appropriately regulate serum mineral balance and tend to retain phosphate that is absorbed from the various dietary components. A high serum level of phosphate is associated with excessive secretion of parathyroid hormone and a tendency to calcification of the soft tissues including the blood vessels.

In dialysis patients, hyperphosphatemia is controlled by removal of phosphate during hemodialysis or peritoneal dialysis. Peritoneal dialysis is a continuous process during which a transfer of phosphates from the blood compartment to the peritoneal fluid occurs relatively efficiently. However, the usual three times a week hemodialysis is not able to remove all the phosphates absorbed and generated during the inter-dialytic interval. Therefore, the majority of patients on the usual three times a week hemodialysis are prescribed agents such as calcium acetate that bind dietary phosphate in the gut, thereby decreasing the absorption of dietary phosphate. It has been shown that increasing the efficiency of dialysis can improve general well-being and overall health of the patient, while preventing complications of kidney failure.

Conventional Hemodialysis (CHD), delivered thrice weekly, results in large biochemical and body fluid volume fluctuations with potentially hazardous peaks and troughs, is still highly unphysiologic. More frequent dialysis schedules may better mimic the normal physiological situation. These include short daily home hemodialysis (SDHD) and slow long-hours nocturnal hemodialysis (NHD) performed 6-10 hours nightly 6-7 times per week. The considerable clinical improvements when patients change to SDHD and NHD dialysis have been almost uniformly observed, and include better well-being and energy, better nutritional indices, higher hemoglobin, better blood-pressure control, much improved intra-dialysis tolerance with fewer cramps, hypotension, nausea, headaches, lesser post dialysis symptoms including fatigue, cramps and lightheadedness. The minor effect of short daily dialysis on phosphate removal-in contrast to the major effect of daily nocturnal dialysis, with its long, 8 hour sessions-probably is related to the complex phosphate kinetics during and after dialysis. After the start of a dialysis session, serum phosphate decreases rapidly to low, though further constant, serum concentrations, only to rise at the end of a 4-hour session. This rapid decrease is caused by an effective phosphate clearance through the dialyzer in the beginning. Thereafter, phosphate starts to be transferred to the blood from extravascular compartment, possibly bone, during the course of a dialysis session, probably due to an active mechanism, triggered by the fall in serum phosphate. This inter-compartmental transfer of phosphate prevents a further decrease in serum phosphate. However, it also determines the rate of phosphate removal during the course of a dialysis session, independent from the type of dialyzer or PTH level. This inter-compartmental transfer can lead to tissue depletion of phosphate.

However, large amounts of phosphate, matching daily intake, can only be removed through long sessions, as in the case of nocturnal hemodialysis. The creation of more "starting periods" with high initial removal rates through frequent dialysis sessions appear to be less effective. The mass balance studies by Al-Hejaili et al. have showed that phosphate removal by NHD (43.5±20.7 mmol) was significantly (P<0.05) higher than by SDHD (24.2±13.9 mmol) but not by CHD (34.0±8.7 mmol) on a per-treatment basis (Al-Hejaili et al. 2003). With the increased frequency of treatments provided by quotidian dialysis, the weekly phosphorus removal (261.2±124.2 mmol) by NHD was significantly higher than by SDHD (P=0.014) and CHD (P=0.03). The highly effective removal of phosphate with NHD not only allows the discontinuation of phosphate binders but in fact, in some patients phosphate has to be added to the dialysate in a concentration of 0.5-4.5 mg/dl in order to prevent the development of hypophosphatemia. In the London Daily/Nocturnal Hemodialysis Study, after being on NHD for a period of 10 months, 2 of the 11 patients needed phosphate supplementation in the dialysate to prevent the development of hypophosphatemia (Lindsay et al. 2003). Furthermore, patients on NHD experience negative calcium balance with increasing serum levels of parathyroid hormone and bone-specific alkaline phosphatase, when a dialysate calcium concentration is 1.25 mmol/L. Hence, dialysate calcium concentration has to be increased to 1.75 mmol/L in NHD patients (Lindsay et al. 2003). Patients have likewise required phosphate supplementation in other studies of NHD. (Lockridge et al. 2001).

In NHD patients requiring phosphate supplementation via the dialysate, as the blood passes through the dialyzer, phosphate is infused concurrently with calcium and bicarbonate since the concentrations of calcium and bicarbonate in the dialysate in NHD patients are 1.5-2.25 mmol/L and 28-35 mEq/L respectively. At the same time, inhibitors of calcification such as pyrophosphate (PPi) and citrate are dialyzed out. This chemical imbalance in the post-dialyzer blood compartment, before it has equilibrated with rest of the blood compartment, is characterized by high calcium and phosphate levels in the presence of an alkaline pH, a microenvironment that is highly conducive to precipitation of calcium in the vessel wall. As this blood enters the heart and bathes the heart valves and the myocardium, there is an increased risk of calcification of the heart valves and the myocardium. The blood is then pumped by the heart into the major vessels and onto the smaller vessels thereby predisposing to calcification of the arterial tree.

A significant proportion of hemodialysis patients have subnormal serum levels of PPi. Serum PPi was below normal (<40 pg/dl) in about 40% of patients with normal serum alkaline phosphatase (n=42) and in about 60% of patients with elevated serum alkaline phosphatase (n=40) (David et al. 1973). Pyrophosphate deficiency may be a risk factor for deposition of calcium into the small vessels of the skin causing an inflammatory vasculitis called calciphylaxis that can lead to gangrene of the skin and underlying tissues, resulting in severe, chronic pain. Calciphylaxis may necessitate amputation of the affected limb and is commonly fatal. There is currently no effective treatment for this condition. Ectopic calcification, if left untreated, results in increased morbidity and death.

Thus, there exists a need for an effective method of maintaining adequate plasma concentrations of calcification inhibitors and inhibiting ectopic calcification in patients with kidney failure undergoing hemodialysis or peritoneal dialysis. The present invention, by administering to the dialysis patient a therapeutic amount of a pyrophosphate via the dialysate satisfies this need and provides related advantages as well.

SUMMARY OF THE INVENTION

The present invention provides a method for replenishing plasma phosphate and/or pyrophosphate in a subject comprising administering into the subject's circulation a therapeutically effective amount of a pyrophosphate. The therapeutically effective amount of a pyrophosphate is most effectively administered intravenously. In preferred embodiments of the present invention, the therapeutically effective amount of a pyrophosphate is administered intravenously by a slow, continuous infusion into the subject, during hemodialysis using an extracorporeal circuit, or during peritoneal dialysis.

It is a further object of this invention to provide a method for replenishing plasma phosphate and/or pyrophosphate in a subject comprising administering a therapeutically effective amount of a pyrophosphate to a subject wherein the pyrophosphate is pyrophosphoric acid or an inorganic or organic salt thereof and the therapeutically effective amount of the pyrophosphate is from about 0.05 micromoles (µmol) to about 45 millimoles (mmol) of pyrophosphate per day, amounts that are equivalent to the amounts of phosphate that are removed during dialysis of a subject.

Yet another object of this invention is to provide a method of preparing a composition for replenishing plasma phosphate and/or pyrophosphate in a subject comprising adding a therapeutically effective amount of a pyrophosphate to a dialysis solution that is to be used to dialyze the subject or to a hemodialysis concentrate. In a preferred embodiment of the present invention, the pyrophosphate is added to a bicarbonate concentrate that is used in the preparation of a hemodialysis solution.

These objects have been achieved by providing liquid or solid compositions for replenishing phosphate and/or pyrophosphate in a subject's plasma comprising a pyrophosphate. The pyrophosphate is pyrophosphoric acid or an inorganic or organic salt thereof and the composition is suitable for addition to a peritoneal dialysate, a hemodialysis solution or a concentrate that is used in the preparation of a hemodialysis solution, most preferably a bicarbonate concentrate. The dialysate composition used to dialyze the patient contains a pyrophosphate in a concentration equivalent to an inorganic phosphorus concentration of 0.5-4.5 mg per deciliter.

In a preferred embodiment of the present invention, a liquid or solid hemodialysis concentrate composition for replenishing phosphate and/or pyrophosphate in a subject's plasma is provided, wherein the pyrophosphate is pyrophosphoric acid or an inorganic or organic salt thereof. In other preferred embodiments of the present invention, a concentrate composition is provided wherein the concentrate composition has a 30- to 50-fold higher pyrophosphate concentration than the final desired concentration of pyrophosphate in the hemodialysate used to dialyze the patient.

Upon further examination of the specification and appended claims, further objects and advantages of the invention will become apparent to those skilled in the art.

DETAILED DESCRIPTION OF THE INVENTION

This invention provides a method to supply phosphate to a subject in need of replenishing the phosphate and/or pyrophosphate in the subject's plasma via a dialysate that contains inorganic phosphorus (Pi) in the form of pyrophosphate (which contains a P—O—P linkage), which is broken down in the body to phosphate by the action of pyrophosphatases such as alkaline phosphatase. Since pyrophosphate (PPi) is an anti-calcific agent, it is able to supplement phosphate without the added risk of calcification. In fact, it may prevent calcification, since the risk of calcification is highly increased in dialysis patients.

The dialysate concentration of pyrophosphate may be determined by the patient's plasma phosphate level. A concentration of 0.5-4.5 mg of inorganic phosphorus (Pi) has to be added per deciliter of dialysate in order to prevent hypophosphatemia. This concentration of can be achieved by addition of a suitable, bio-available salt of pyrophosphate (PPi) such as sodium ($Na_4P_2O_7$ or $Na_2H_2P_2O_7$), potassium, calcium or magnesium pyrophosphate or as pyrophosphoric acid ($H_4O_7P_2$, contains 35% Pi by weight).

Pyrophosphoric acid and its salts are soluble in water. The solubility of pyrophosphoric acid at room temperature is about 700 g/100 ml of water. The addition of PPi to the acid hemodialysis concentrate results in formation of a precipitate. Therefore, PPi is not compatible with the acid concentrate that is used to prepare hemodialysis solutions. On the other hand, pyrophosphoric acid and pyrophosphate salts are freely soluble in the bicarbonate concentrate that is used to prepare hemodialysis solutions. Therefore, it is feasible to achieve requisite levels of PPi in the dialysate by addition of 30-50 fold higher levels to the bicarbonate concentrate. Similarly, PPi can be added to peritoneal dialysis solutions that are used by patients on peritoneal dialysis in order to prevent phosphate depletion and/or prevent calcification.

PPi is readily dialyzable across hemodialysis membranes since the molecular weight of pyrophosphate anion is only about 175 Dalton. The clearance or dialysance of PPi exceeds that of creatinine using a coil kidney. Consequently, there is a rapid decline in serum PPi during dialysis. When PPi is added to the dialysate in a concentration that exceeds the PPi concentration in the plasma, there is rapid transfer from the dialysate to the blood compartment. The dialysance of PPi by modern high efficiency or high flux dialyzer membranes has not been reported but is expected to be highly efficient.

Pyrophosphate (PPi) is known to be a potent inhibitor of calcification. PPi is used as anti-scaling additives in washing powders, water and oil brines to prevent calcium carbonate scales. Furthermore, it is one of the main anti-tartar agents in toothpastes world-wide. Therefore, it is reasonable to expect that dialysate solutions comprising pyrophosphate may help preserve the hollow fiber hemodialysis membranes, thereby prolonging the life of membranes and increasing reuse.

The role of pyrophosphate in inhibition of calcification has been studied extensively in vitro and in human and animal studies (Fleisch et al. 1965). PPi in a concentration as low as 0.1 μM can bind strongly to crystals of hydroxyapatite, thereby inhibiting further precipitation of calcium phosphate. The normal concentration of PPi in human plasma of 2-4 μm/L is within the range at which a strong inhibition of calcium phosphate precipitation is observed in vitro even in the presence of nucleating substances, such as collagen. PPi at a 2 μm/L concentration is rapidly and almost completely taken up by the apatite crystals. The rapidity of the binding reaction suggests that PPi binds predominantly to the surface of apatite crystals. PPi is present mainly in the high ratio shell and/or the surface layer of the crystals where it displaces orthophosphate. Electron microscopy and x-ray diffraction analysis have shown that there is no increase in crystals size when PPi coats the apatite crystals even from solutions highly super saturated with calcium and phosphate. The inhibition of calcification by PPi has been explained as a blockage of crystal growth centers by adsorption of the compound onto the apatite crystals at sites of calcification. Fleisch and co-workers have reported that PPi inhibits calcification in aortas and kidneys of rats treated with large amount of vitamin $D_3$ (Fleisch et al. 1965). Therefore, plasma PPi is critical in preventing precipitation.

In dialysis patients, a therapeutically effective amount of pyrophosphate anions, either as an acid or a functional salt thereof, can be administered either intravenously or by slow continuous intravenous infusion or via the hemodialysis or peritoneal dialysis solution. The method consists of administering a therapeutically effective amount of pyrophosphate, thereby replenishing plasma phosphate and/or pyrophosphate levels. Furthermore, an effective amount of pyrophosphate is added to the dialysis solution used to dialyze the said hemodialysis or peritoneal dialysis patient, thereby effectively replenishing plasma phosphate and/or pyrophosphate levels.

The therapeutic level of PPi in the dialysate may vary from μM to mM range, depending on the following factors 1. Patient related factors including serum PPi and Pi levels, body weight, presence or absence of calcification, and other bone and mineral parameters such as bone alkaline phosphatase and parathyroid hormone levels,
2. Modality of dialysis: hemodialysis versus peritoneal dialysis, duration of dialysis (conventional versus daily versus slow nocturnal, CAPD versus CCPD), dialysis vintage.
3. Clinical indication: treatment versus prevention of hypophosphatemia versus hypo-pyrophosphatemia, prevention versus treatment of vascular calcification, severity of vascular calcification (asymptomatic vs. calciphylaxis/gangrene).

References:

Al-Hejaili F, Kortas C, Leitch R, et al. Nocturnal but not short hours quotidian hemodialysis requires an elevated dialysate calcium concentration. J Am Soc Nephrol 2003; 14 (9):2322-8.

David D S, Sakai S, Granda J, et al. Role of pyrophosphate in renal osteodystrophy. Transactions—American Society for Artificial Internal Organs 1973; 19:440-5.

Fleisch H, Schibler D, Maerki J, et al. Inhibition of aortic calcification by means of pyrophosphate and polyphosphates. Nature 1965; 207 (3):1300-1.

Lindsay R M, Alhejaili F, Nesrallah G, et al. Calcium and phosphate balance with quotidian hemodialysis. Am J Kidney Dis 2003; 42 (1 Suppl):24-9.

Lockridge R S, Jr., Spencer M, Craft V, et al. Nocturnal home hemodialysis in North America. Adv Ren Replace Ther 2001; 8 (4):250-6.

I claim:

1. A method for the replenishment of plasma phosphate in a subject in need thereof, said method comprising parenterally administering directly to the subject in need of replenishment of plasma phosphate a liquid composition comprising a compound selected from the group consisting of pyrophosphoric acid, an organic pyrophosphate, calcium pyrophosphate, magnesium pyrophosphate, sodium pyrophosphate, and potassium pyrophosphate in an amount that is therapeutically effective for the replenishment of plasma phosphate, said compound being in the directly administered composition at a concentration equivalent to an inorganic phosphorus concentration in the range of 0.5 to 4.5 mg per deciliter.

2. The method of claim 1 wherein the compound is administered intravenously.

3. The method of claim 2 wherein the compound is administered intravenously by a slow, continuous infusion into the subject.

4. The method of claim 1 wherein the composition is a hemodialysis solution and the compound is administered to a subject during hemodialysis by inclusion of the compound in the hemodialysis solution used to hemodialyze the subject.

5. The method of claim 4 wherein the hemodialysis solution has been prepared by adding the compound to a bicarbonate concentrate which was used to make the hemodialysis solution.

6. The method of claim 1 wherein the composition is a peritoneal dialysis and the compound is administered to the peritoneal cavity of a subject during peritoneal dialysis by inclusion of the compound in a peritoneal dialysis solution used to dialyze the subject.

* * * * *